United States Patent [19]
Lauf et al.

[11] Patent Number: 5,367,283
[45] Date of Patent: Nov. 22, 1994

[54] THIN FILM HYDROGEN SENSOR

[75] Inventors: Robert J. Lauf, Oak Ridge; Barbara S. Hoffheins, Knoxville; Pamela H. Fleming, Oak Ridge, all of Tenn.

[73] Assignee: Martin Marietta Energy Systems, Inc., Oak Ridge, Tenn.

[21] Appl. No.: 957,337

[22] Filed: Oct. 6, 1992

[51] Int. Cl.$^5$ .............................................. H01C 7/00
[52] U.S. Cl. .................................... 338/34; 422/90; 73/31.05; 338/307; 338/320
[58] Field of Search .................... 338/34, 35, 306, 307, 338/319, 320; 437/153; 73/31.01, 31.05, 31.06; 422/90

[56] References Cited
U.S. PATENT DOCUMENTS 3,559,457  2/1971  Collins ................................. 73/23
4,624,137 11/1986  Johnson et al. ................. 338/319 X
4,931,851  6/1990  Sibbald et al. ...................... 357/25

OTHER PUBLICATIONS

M. A. Butler and D. S. Ginley, "Hydrogen Sensing with Palladium-Coated Optical Fibers," *J. Appl Phys.*, vol. 64, No. 7, 1 Oct. '88, pp. 3706–3712.

P. A. Michaels, "Design, Development and Prototype Fabrication of an Area Hydrogen Detector (5 Apr. 1963 through 4 Apr. 1964)," Summary Report Submitted to George C. Marshall Space Flight Center, Huntsville, Ala., by The Bendix Corporation, Research Laboratories Div., Southfield, Michigan, Sep. 1964.

P. J. Shaver, "Bimetal Strip Hydrogen Gas Detectors," *The Review of Scientific Instruments*, vol. 40, No. 7, Jul. 1969, pp. 901–905.

*Primary Examiner*—Marvin M. Lateef
*Attorney, Agent, or Firm*—Joseph A. Marasco; J. Kenneth Davis; Harold W. Adams

[57] ABSTRACT

A hydrogen sensor element comprises an essentially inert, electrically-insulating substrate having a thin-film metallization deposited thereon which forms at least two resistors on the substrate. The metallization comprises a layer of Pd or a Pd alloy for sensing hydrogen and an underlying intermediate metal layer for providing enhanced adhesion of the metallization to the substrate. An essentially inert, electrically insulating, hydrogen impermeable passivation layer covers at least one of the resistors, and at least one of the resistors is left uncovered. The difference in electrical resistances of the covered resistor and the uncovered resistor is related to hydrogen concentration in a gas to which the sensor element is exposed.

22 Claims, 5 Drawing Sheets

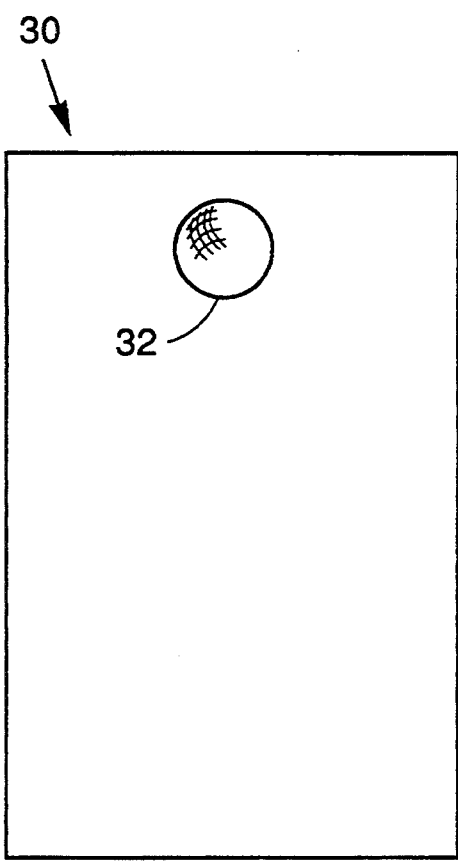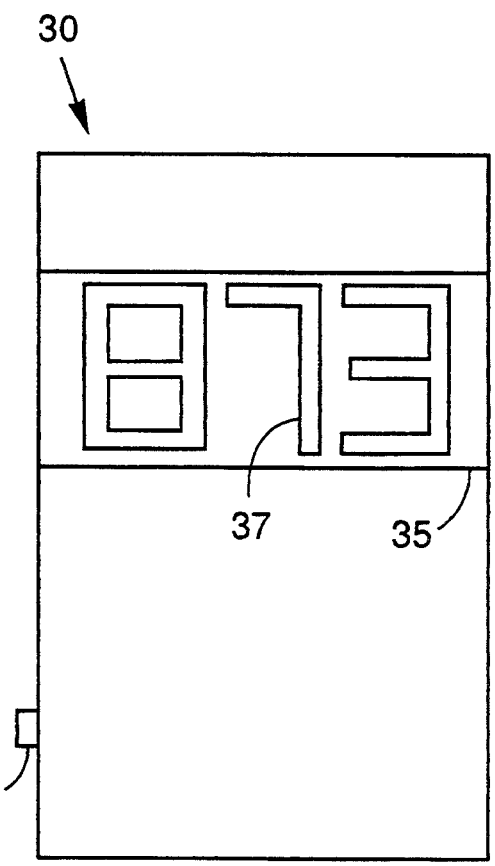
FIG. 4      FIG. 5

THIN FILM HYDROGEN SENSOR

The United States Government has rights in this invention pursuant to contract no. DEAC05-84OR21400 between the United States Department of Energy and Martin Marietta Energy Systems, Inc.

FIELD OF THE INVENTION

The present invention relates to devices and methods for monitoring the composition of gases and, more particularly, to solid state devices incorporating palladium (Pd) metal films, and methods relating thereto for measuring hydrogen concentration in a gas composition.

BACKGROUND OF THE INVENTION

In the field of gas sensing and analysis, it is well known that when Pd metal is exposed to hydrogen gas, hydrogen molecules dissociate on the Pd surface and the resulting hydrogen atoms can diffuse into the bulk of the Pd, eventually reaching an equilibrium concentration in the metal. It is therefore possible to measure the gaseous concentration of hydrogen by measuring one or more of the physical properties of Pd that are influenced by dissolved hydrogen.

Methods are to measure the physical expansion of a known length of Pd rod (R. L. Collins, Hydrogen Detector, U.S. Pat. No. 3,559,457), the deflection of a bimetallic strip (P. J. Shaver, Bimetal Strip Hydrogen Gas Detectors, The Rev. of Sci. Instru. 40 [7], 901–5, 1969), or the elongation of a Pd-coated optical fiber (M. A. Butler and D. S. Ginley, Hydrogen Sensing with Pd-Coated Optical Fibers, J. Appl. Phys. 64 [7], 3706–12, 1988).

Another technique is to measure changes in the electrical resistivity of a Pd thin film (P. A. Michaels, Design, Development, and Prototype Fabrication of an Area Hydrogen Detector, Bendix Corporation, Southfield, Mich., 1964, Contract NAS8-5282). Because the resistance changes are small, it is necessary to amplify the signal and, at the same time, to provide temperature compensation. Michaels, therefore, used two rectangular Pd thin films, deposited side-by-side on a glass slide. The film dimensions were such that each strip had a resistance of about 10 $\Omega$. One strip was covered by a thin layer of silicone resin or Mylar tape, and the other was uncovered. An external circuit was constructed such that the two strips formed the passive and active legs, respectively, of a Wheatstone resistance bridge.

The hydrogen sensor described by Michaels had several limitations. Firstly, the Pd was deposited directly onto the glass substrate, and adhesion thereto was not sufficient for use in a practical device, particularly at high hydrogen concentrations. High concentrations of hydrogen generally lead to appreciable mechanical strain in the Pd film and cause it to peel away from the substrate. Secondly, the two-element bridge required external bridge resistors and cumbersome electronics which would make a practical device more difficult to produce. The external resistors very often are variable resistors so that one can adjust them to bring the bridge into balance at some reference condition (e.g., to give a zero reading when no hydrogen is present). These external circuits are usually cumbersome and a source of noise in the output signal. Furthermore, when the active and passive metallizations are configured as two parallel rectangles, their resistance is generally undesirably low in a sensor of any practical size. This in turn requires either a large current in the bridge or a very sensitive amplifier. Furthermore, the low aspect ratio of the Pd strips (L/W$\simeq$10) and their correspondingly low resistance (10$\Omega$) leads to high power consumption and inefficient amplification, which would make a practical device more difficult to operate.

Finally, the use of polymer films as the passivation layer is incompatible with high temperature or hostile environment applications, severely limiting the usefulness of a practical device.

OBJECTS OF THE INVENTION

Accordingly, among the objects and advantages of the present invention is the provision of a new and improved hydrogen detecting device having a thin-film Pd hydrogen sensing element with enhanced adhesion and robustness. The device is lightweight and portable, exhibits low power consumption, is capable of functioning at relatively high concentrations such as the explosive limit in air (4%), is useful in hostile environments and at high temperatures, and exhibits an improved signal-to-noise ratio.

Further and other objects and advantages of the present invention will become apparent from the description contained herein.

SUMMARY OF THE INVENTION

In accordance with one aspect of the present invention, the foregoing and other objects are achieved by a hydrogen sensor element which comprises an essentially inert, electrically-insulating substrate; a thin-film metallization deposited on the substrate, the metallization forming at least two resistors on the substrate, the metallization comprising a layer of Pd or a Pd alloy for sensing hydrogen and an underlying intermediate metal layer for providing enhanced adhesion of the metallization to the substrate; and an essentially inert, electrically insulating, hydrogen impermeable passivation layer covering at least one of the resistors at least one of the resistors being left uncovered, the difference in electrical resistances of the covered resistor and the uncovered resistor being related to hydrogen concentration in a gas to which the sensor element is exposed.

In accordance with another aspect of the present invention, a hydrogen sensor element comprises an essentially inert, electrically-insulating substrate; a thin-film metallization deposited on the substrate, the metallization forming four resistors in a Wheatstone resistance bridge arrangement, the metallization comprising a first intermediate metal layer deposited on the substrate for providing enhanced adhesion of the metallization to the substrate, a second intermediate metal layer deposited on the first intermediate metal layer for passivating the first intermediate metal layer, and a layer of Pd or a Pd alloy deposited on the second intermediate metal layer for sensing hydrogen; and an essentially inert, electrically insulating, hydrogen impermeable passivation layer covering at least one of the resistors.

In accordance with a further aspect of the present invention, an apparatus for detecting hydrogen comprises a hydrogen sensor element comprising an essentially inert, electrically-insulating substrate; a thin-film metallization deposited on the substrate, the metallization forming at least two resistors on the substrate, the metallization comprising a layer of Pd or a Pd alloy for sensing hydrogen and an underlying intermediate metal layer for providing enhanced adhesion of the metallization to the substrate; and an essentially inert, electrically insulating, hydrogen impermeable passivation layer covering at least one of the resistors, at least one of the resistors being left uncovered, the difference in electrical resistances of the covered resistor and the uncovered resistor being related to hydrogen concentration in a gas to which the sensor element is exposed; a power supply means for applying a fixed voltage to the resistance bridge; and a measuring means for detecting and measuring the difference in electrical resistances.

BRIEF DESCRIPTION OF THE DRAWING

In the drawings:

FIG. 4 is a rear view of the apparatus shown in FIG. 3.

FIG. 5 is a front view of the apparatus shown in FIG. 3.

For a better understanding of the present invention, together with other and further objects, advantages and capabilities thereof, reference is made to the following disclosure and appended claims in connection with the above-described drawings.

DETAILED DESCRIPTION OF THE INVENTION

Figure 1:
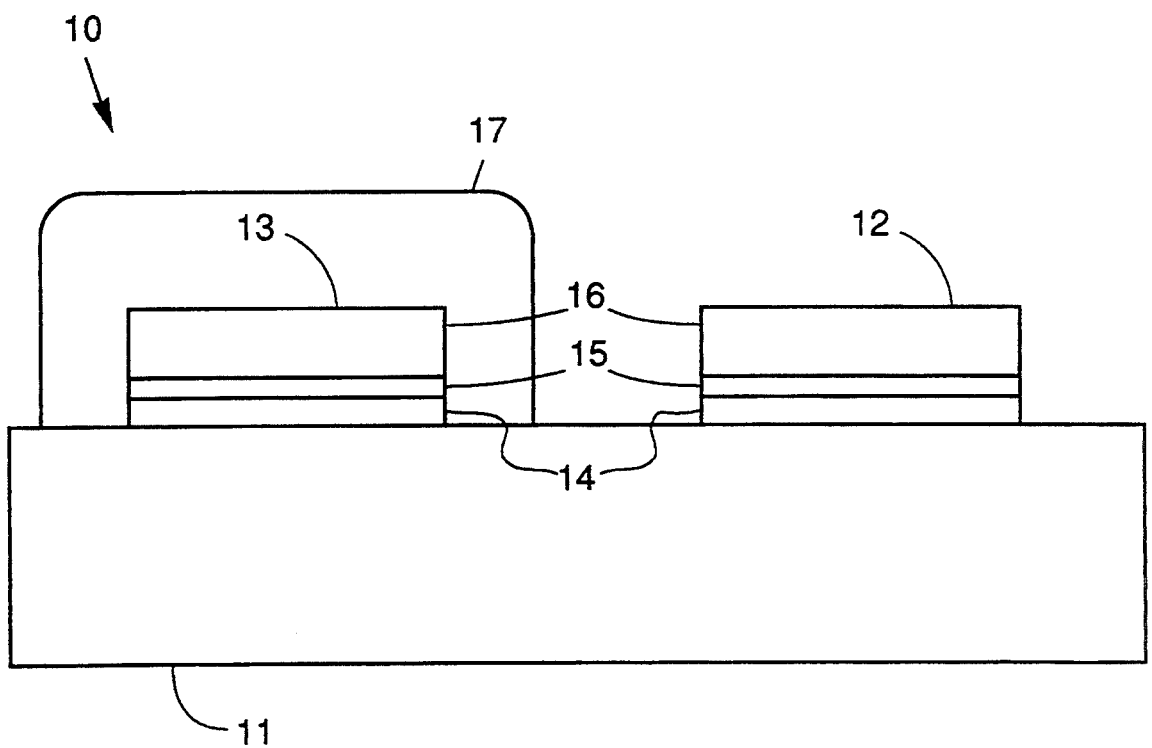
FIG. 1 is a schematic cross sectional side view showing the layers of a hydrogen sensing element having two multilayer metallizations on an inert substrate; one metallization is covered and the other metallization is exposed.

Referring firstly to FIG. 1, in a preferred embodiment of the present invention, a simplified hydrogen sensor element 10 comprises multilayer metallizations 12, 13 deposited on a relatively inert substrate 11 comprised of silicon, glass, quartz, mica, ceramics, or porcelain.

In accordance with the invention, intermediate layers 14, 15 are deposited on the substrate 11 prior to depositing the hydrogen sensing Pd or Pd alloy layer 16. A first intermediate layer 14 is chosen for enhanced adhesion to the substrate 11. A second intermediate layer 15 is applied if necessary to passivate the first intermediate layer 14, i.e., to prevent interactions between the first intermediate layer 14 and the Pd layer 16, or to prevent the first intermediate layer 14 from absorbing hydrogen dissolved in the Pd layer 16.

The metal used for the first intermediate layer 14 depends to some extent on the choice of substrate 11. For example, a first intermediate layer 14 of titanium is a suitable for improving adhesion to an alumina substrate 11 whereas a first intermediate layer 14 of chromium is suitable for improving adhesion to silica or glass substrate 11. Suitable metals for the first intermediate layer 14 include Ti, Cr, Nb, Hf, Mo, Zr, alloys thereof, and the like.

Because reactive metals such as titanium can irreversibly absorb hydrogen from the Pd layer 16, it is desirable to deposit onto the first intermediate layer 14 a second intermediate layer 15 for inactivating the underside of the Pd layer 16. The second intermediate layer 15 preferably comprises a metal with very low hydrogen solubility such as Au, Ag, Pt, Rh, Ni, alloys thereof, and the like. The Pd layer 16 is deposited onto the second intermediate layer 15.

In order to minimize the effect of electrical conduction in intermediate layers 14, 15, their thicknesses should be much less than that of the Pd layer 16. All the metallization layers 14, 15, 16 are easily deposited on the substrate through a single photomask using well known conventional techniques.

A hydrogen-impermeable passivating layer 17 is deposited through a second photomask; it must be large enough to completely cover the top and edges of the covered metallization 13 in order to prevent hydrogen absorption thereby. The passivating layer 17 can be any essentially inert, electrically insulating material, usually a ceramic, characterized by low permeability to hydrogen, that can be deposited in a layer having adequate thickness and density. The passivating layer 17 can be deposited by any suitable conventional technique such as sputtering or chemical vapor deposition.

During exposure to analyte gases, the resistance of the uncovered, exposed metallization 12 is compared to that of a covered, unexposed metallization 13 in order to eliminate the effects of temperature changes on resistivity. The resistance difference between the exposed metallization 12 and unexposed metallization 13 can be easily measured. The familiar Wheatstone Bridge technique is preferred, wherein an imbalance in the resistance bridge is measured.

Figure 2:
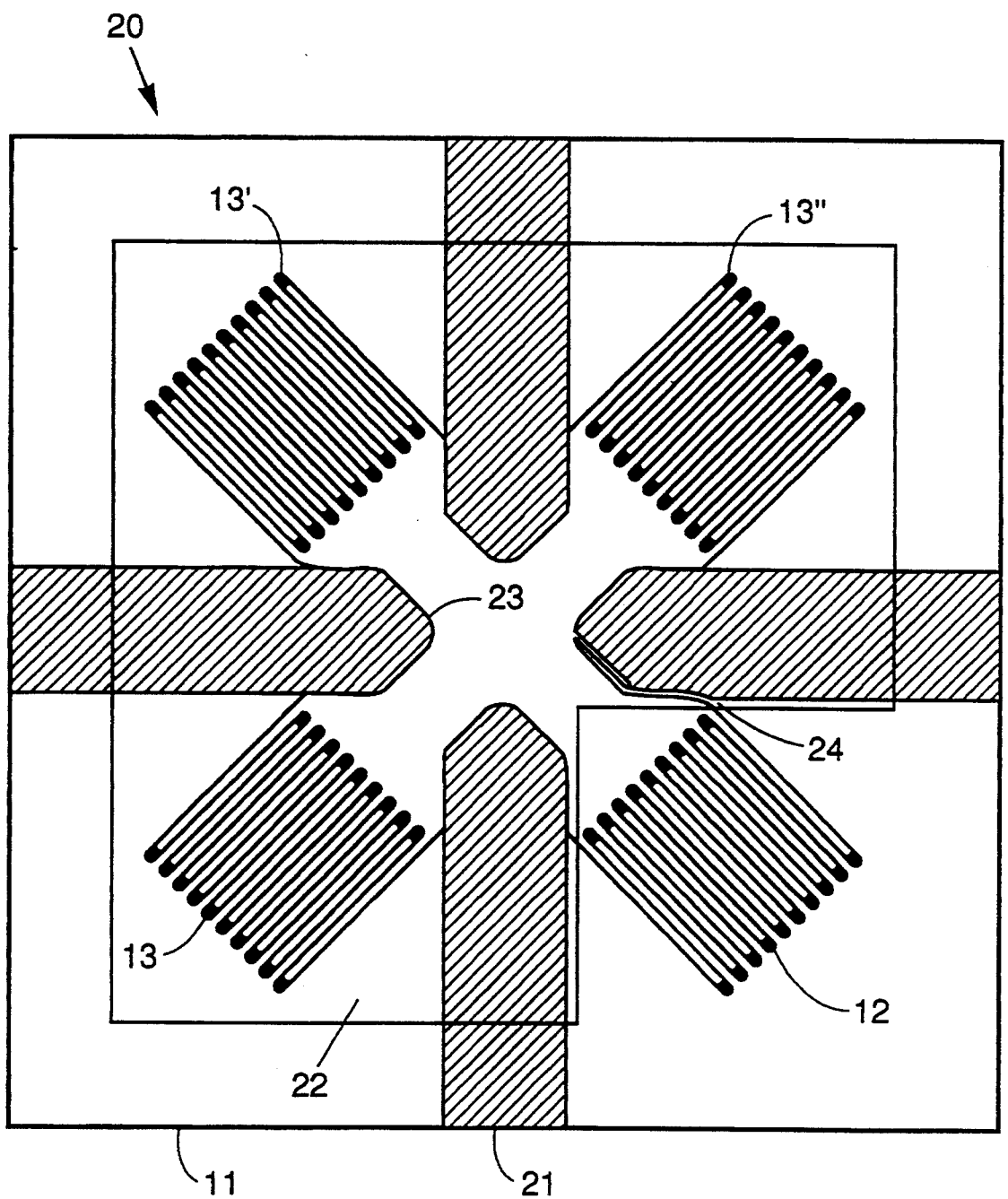
FIG. 2 is a plan view of a hydrogen sensing element having a bridge circuit comprising four sinuous resistors, three of which are covered by a passivating layer.

Referring now to FIG. 2, in a preferred embodiment of the present invention, a practical sensor element 20 incorporates all four resistor legs of a Wheatstone resistance bridge (one uncovered metallization 12 and three identical covered metallizations 13, 13', 13") deposited in a single monolithic metallization pattern 21, and having deposited thereon a single passivating layer 22 covering the covered metallizations 13, 13', 13". The single passivating layer 22 is shown in FIG. 2 as a border outline in order to illustrate clearly all aspects of the metalization 21. Large interconnections 23 are provided for ease in connecting the sensor element 20 to other components in a detecting instrument.

The sinuous pattern of the metallizations 12, 13, 13', 13" greatly increases their aspect ratios and electrical resistance. A suggested aspect ratio would be of at least $L/W \approx 100$, more preferably $L/W \approx 400$. Specific aspect ratios and electrical resistance values are not critical to the practice of the invention, and these values can be varied by the skilled artisan for optimal performance under a given set of circumstances.

A further advantage of the large interconnections 23 is the ability to trim the pattern by cutting lines 24 by laser or other means. In this way, the resistances of all four bridge resistors can be balanced during the manufacturing process, eliminating the need for external variable resistors.

Figure 3:
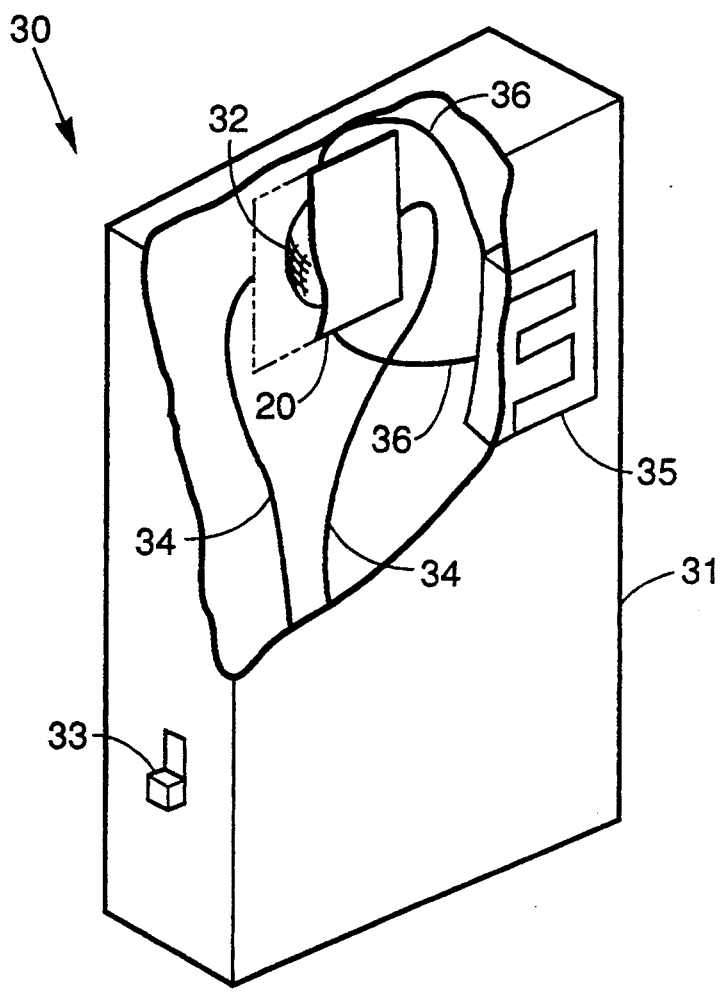
FIG. 3 is a cutaway oblique view of a portable, battery-powered hand-held hydrogen sensing apparatus showing the sensor element and digital voltage display.

FIGS. 3, 4 and 5 show various views of a small, battery-powered hydrogen detector 30 constructed in accordance with the present invention. Contained within a plastic or metal case 31, the hydrogen sensor element 20 is placed directly behind an opening 32 which is preferably covered with a wire mesh screen in order to protect the sensor element 20 and prevent ignition in high concentrations of hydrogen. Switch 33 is activated to apply voltage from a battery (normally 9 V, not shown) across the resistance bridge on the sensor element 20 through a first circuit formed by two wires 34.

Orientation of the sensor element 20 is not critical as to the position of the resistor which is left uncovered for absorbing hydrogen. The voltage difference between the active and passive bridge elements on the sensor element 20 is measured by a digital voltmeter 35 through a second circuit formed by two wires 36, and thereby displayed digitally 37. Depending on the orientation of the sensor element 20, a positive or negative voltage difference will be measured.

EXAMPLE I

A sensor element having the metallization pattern shown in FIG. 2 was fabricated by vapor deposition on a 1 inch square alumina substrate. The first intermediate layer was titanium, deposited to a thickness of about 50–100 Å. The second intermediate layer was gold, deposited to a thickness of about 50–100 Å thick. Pd was then deposited to a thickness of about 1000–2000 Å thick. Using the method described above, the resistance of each leg of the Wheatstone resistance bridge was balanced with the others, at about 400 Ω. A passivation layer of silica was deposited to a thickness of about 500 Å. During initial testing, it was determined that the silica layer was not completely impermeable by noting that after a 20 minute exposure to a gas mixture of Argon containing about 4% $H_2$ (Ar-4% $H_2$), the output voltage of the bridge began to fall indicating a slow penetration of hydrogen into the "passive" legs. Also, when the test gas was removed and the sensor element returned to equilibrium with air, there was an initial "undershoot" of the output voltage, again indicating the presence of some hydrogen in the passive legs which took longer to diffuse into the air.

EXAMPLE II

Figure 6:
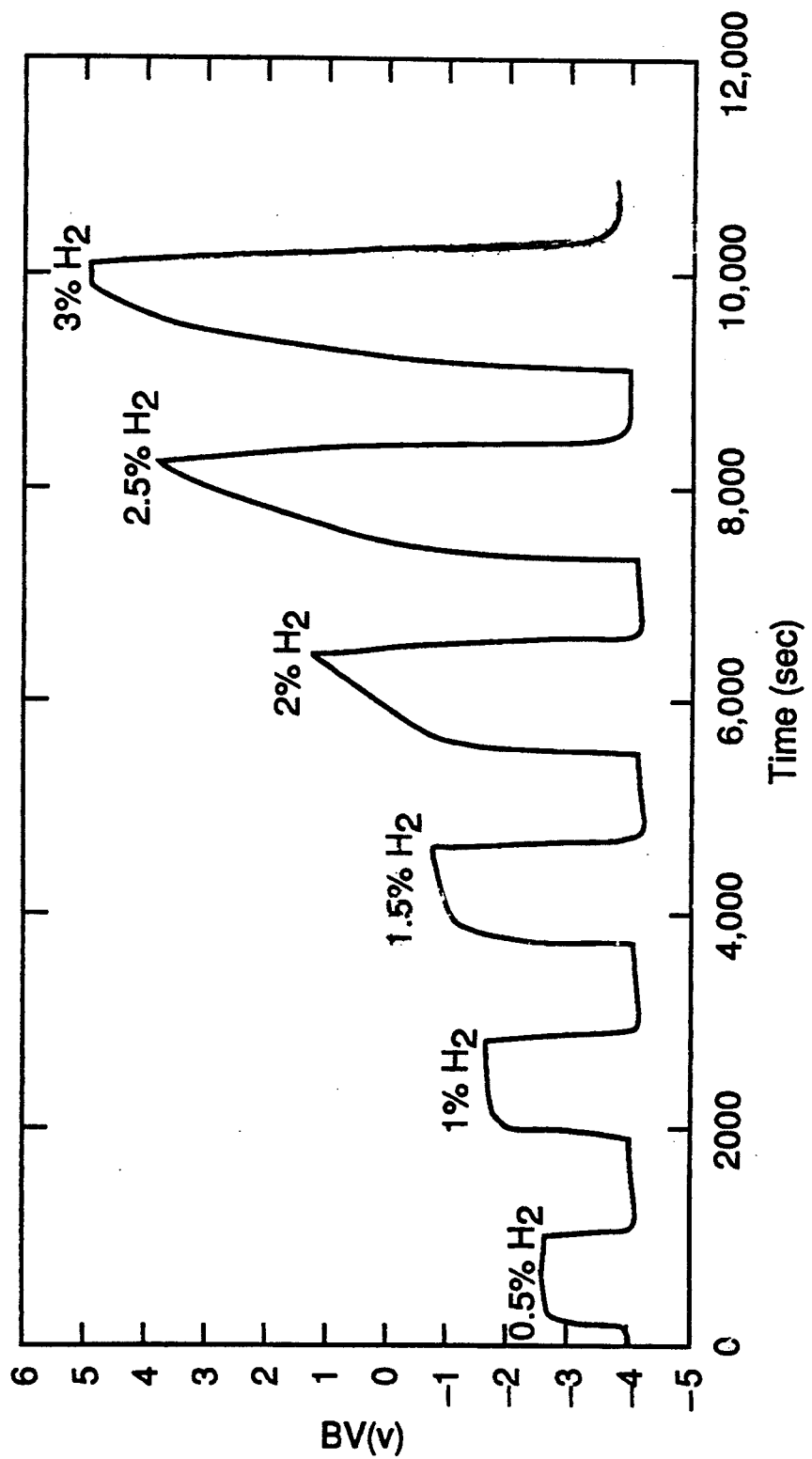
FIG. 6 is a graph showing the output of the hydrogen detector during exposure to various concentrations of hydrogen gas.

The permeability of the passivation layer of the sensor element of Example I was greatly reduced by applying to the silica passivation layer a lacquer coating having a thickness of about 250 μm. FIG. 6 shows the response, in mV, of the lacquer coated sensor element upon exposure to various concentrations of hydrogen, from about 0.5% to about 3% in air. The sensor output increased with increasing hydrogen concentration.

EXAMPLE III

Several sensor elements were fabricated as described in Example I, but with a thicker silica layer of about 1000 to about 2000 Å. These sensor elements performed well without the need for a lacquer overlayer. In all cases, no delamination or other deterioration of the Pd film was observed upon exposure to the Ar-4% $H_2$, even after saturation. This indicates the effectiveness of the titanium and gold layers for insuring adhesion and resisting mechanical strains caused by absorption of hydrogen into the Pd layer.

EXAMPLE IV

A sensor element was fabricated as described in Example I, but with a passivation layer of $Ta_2O_5$, about 1500 Å thick. The performance of this sensor element at room temperature was similar to that of Example III. With 9 V applied to the bridge, exposure of the element to Ar-4% $H_2$ produced an output signal in excess of 2 V with no amplification other than the inherent amplifying effect of the bridge itself.

EXAMPLE V

The sensor element described in Example IV was tested at elevated temperatures by applying 300 to 700 mW to a resistance heater placed under the alumina substrate to produce temperatures ranging from about 20° to about 70° C. The sensor behaved reproducibly at any temperature tested, although the behavior at high temperatures is somewhat different from that at room temperature, presumably because of the reduced hydrogen concentration and greater surface reactivity in the former case. At elevated temperatures, for a given hydrogen concentration in the gas phase, the sensor responded faster, but the steady-state output signal was lower.

EXAMPLE VI

The sensor element was fabricated as described in Example IV, but coated with a passivation layer of $MgF_2$ approximately 2000 Å thick. This sensor responded similarly to the above described sensor elements when exposed to Ar-4% $H_2$.

EXAMPLE VII

A hydrogen detecting instrument was constructed as shown in FIG. 3. The entire instrument is contained within a conventional plastic case having nominal dimensions of about 3×5-½×1-½". The sensor element was mounted behind a 0.6" diameter opening on the rear side of the case, covered with wire mesh to protect the sensor and prevent ignition. A sensor element of the type described in Example III was mounted directly behind the opening. Output signal was displayed by a digital panel meter mounted in the front of the case. The digital panel meter used was an Acculex DP-176BL (Metrabyte, Taunton, Mass.) set for ±2 V full scale. Two 9 V dry cell batteries were used, one providing working voltage to the bridge circuit and the other providing power to operate the digital panel meter. The entire unit was portable and weighed less than 20 ounces.

EXAMPLE VIII

The hydrogen detecting instrument described in Example VII was exposed to air; the panel display was 9 mV. When exposed to a stream of Ar-4% $H_2$, the panel display responded with increased voltage readings in about five seconds, and after one minute the reading was 100 mV.

The hydrogen detecting instrument described herein is particularly useful as a fast responding, portable device to detect hydrogen leaks in tanks and piping, and to detect a buildup of hydrogen in areas around batteries, plating tanks, furnaces, hydrogen production facilities, chemical processing facilities, etc.

While there has been shown and described what are at present considered the preferred embodiments of the invention, it will be obvious to those skilled in the art that various changes and modifications can be made therein without departing from the scope of the inventions defined by the appended claims.

What is claimed is:

1. A hydrogen sensor element comprising:
   an essentially inert, electrically-insulating substrate;
   a thin-film metallization deposited on said substrate, said metallization forming at least two resistors on said substrate, said metallization comprising a layer of Pd or a Pd alloy for sensing hydrogen and an underlying intermediate metal layer for providing enhanced adhesion of said metallization to said substrate; and an essentially inert, electrically insulating, hydrogen impermeable passivation layer covering at least one of said resistors, at least one of said resistors being left uncovered, the difference in electrical resistances of said covered resistor and said uncovered resistor being related to hydrogen concentration in a gas to which said sensor element is exposed.

2. A hydrogen sensor element according to claim 1 wherein said substrate comprises a material selected from the group consisting of silicon, glass, quartz, mica, ceramic, and porcelain enamel.

3. A hydrogen sensor element according to claim 1 wherein said intermediate metallization layer comprises a metal selected from the group consisting of Ti, Cr, Nb, Hf, Mo, and Zr.

4. A hydrogen sensor element according to claim 1 wherein said passivation layer comprises a material selected from the group consisting of $MgF_2$, $CaF_2$, $MgO$, $SiO_2$, $Si_3N_4$, $Al_2O_3$, $AlN$, $BN$, and $Ta_2O_5$.

5. A hydrogen sensor element according to claim 1 wherein said metallization comprises four resistors in a Wheatstone resistance bridge arrangement, said four resistors having aspect ratios of at least $L/W \simeq 100$, and four interconnections of sufficient size to allow each of said four resistors to be trimmed in order to balance said Wheatstone resistance bridge arrangement, said passivation layer covering three of said resistors.

6. A hydrogen sensor element according to claim 1 wherein said substrate comprises $Al_2O_3$, wherein said intermediate metallization layer comprises Ti, and wherein said passivation layer comprises $SiO_2$.

7. A hydrogen sensor element according to claim 1 wherein said substrate comprises $Al_2O_3$, wherein said intermediate metallization layer comprises Ti, and wherein said passivation layer comprises $MgF_2$.

8. A hydrogen sensor element according to claim 1 wherein said substrate comprises $Al_2O_3$, wherein said intermediate metallization layer comprises Ti, and wherein said passivation layer comprises $Ta_2O_5$.

9. A hydrogen sensor element comprising:
an essentially inert, electrically-insulating substrate;
a thin-film metallization deposited on said substrate, said metallization forming four resistors in a Wheatstone resistance bridge arrangement, said metallization comprising a first intermediate metal layer deposited on said substrate for providing enhanced adhesion of said metallization to said substrate, a second intermediate metal layer deposited on said first intermediate metal layer for passivating said first intermediate metal layer, and a layer of Pd or a Pd alloy deposited on said second intermediate metal layer for sensing hydrogen; and
an essentially inert, electrically insulating, hydrogen impermeable passivation layer covering at least one of said resistors.

10. A hydrogen sensor element according to claim 9 wherein said substrate comprises a material selected from the group consisting of silicon, glass, quartz, mica, ceramic, and porcelain enamel.

11. A hydrogen sensor element according to claim 9 wherein said first intermediate metallization layer comprises a metal selected from the group consisting of Ti, Cr, Nb, Hf, Mo, and Zr.

12. A hydrogen sensor element according to claim 9 wherein said second intermediate metallization layer comprises a metal selected from the group consisting of Au, Ag, Pt, Rh, and Ni.

13. A hydrogen sensor element according to claim 9 wherein said substrate comprises $Al_2O_3$, wherein said first intermediate metallization layer comprises Ti, said second intermediate metallization layer comprises Au, and wherein said passivation layer comprises $SiO_2$.

14. A hydrogen sensor element according to claim 9 wherein said substrate comprises $Al_2O_3$, wherein said first intermediate metallization layer comprises Ti, said second intermediate metallization layer comprises Au, and wherein said passivation layer comprises $MgF_2$.

15. A hydrogen sensor element according to claim 9 wherein said substrate comprises $Al_2O_3$, wherein said first intermediate metallization layer comprises Ti, said second intermediate metallization layer comprises Au, and wherein said passivation layer comprises $Ta_2O_5$.

16. A hydrogen sensor element according to claim 9 wherein said metallization comprises four resistors in a Wheatstone resistance bridge arrangement, said four resistors having aspect ratios of at least $L/W \simeq 100$, and four interconnections of sufficient size to allow each of said four resistors to be trimmed in order to balance said Wheatstone resistance bridge arrangement.

17. A hydrogen sensor element according to claim 9 wherein said passivation layer comprises a material selected from the group consisting of $MgF_2$, $CaF_2$, $MgO$, $SiO_2$, $Si_3N_4$, $Al_2O_3$, $AlN$, $BN$, and $Ta_2O_5$.

18. An apparatus for detecting hydrogen comprising:
a hydrogen sensor element comprising an essentially inert, electrically-insulating substrate; a thin-film metallization deposited on said substrate, said metallization forming at least two resistors on said substrate, said metallization comprising a layer of Pd or a Pd alloy for sensing hydrogen and an underlying intermediate metal layer for providing enhanced adhesion of said metallization to said substrate; and an essentially inert, electrically insulating, hydrogen impermeable passivation layer covering at least one of said resistors, at least one of said resistors being left uncovered, the difference in electrical resistances of a said covered resistor and said uncovered resistor being related to hydrogen concentration in a gas to which said sensor element is exposed;
a power supply means for applying a fixed voltage to said resistance bridge; and
a measuring means for detecting and measuring said difference in electrical resistances.

19. The apparatus of claim 18 wherein said intermediate metal layer is a first intermediate metal layer deposited on said substrate, wherein said metallization further comprises a second intermediate metal layer deposited on said first intermediate metal layer for passivating said first intermediate metal layer, and wherein said layer of Pd or a Pd alloy is deposited on said second intermediate metal layer.

20. The apparatus of claim 18 wherein a plurality of said hydrogen sensor elements are distributed among various locations and communicate with a central instrument which monitors the outputs of said plurality of sensors and displays the hydrogen concentrations at said locations.

21. The apparatus of claim 18 wherein said measuring means further comprises means for providing indicia displaying said voltage imbalance as an indication of the presence of hydrogen.

22. The apparatus of claim 18 wherein said resistors form at least part of a resistance bridge, and wherein said measuring means detects and measures a voltage imbalance of said resistance bridge.

* * * * *